(12) United States Patent
Deforche (10) Patent No.: US 11,302,418 B2
(45) Date of Patent: Apr. 12, 2022

(54) ALIGNMENT METHOD FOR NUCLEIC ACID SEQUENCES

(71) Applicant: Emweb bvba, Herent (BE)

(72) Inventor: Koen Deforche, Kessel-Lo (BE)

(73) Assignee: Emweb bvba, Herent (BE)

( * ) Notice: Subject to any disclaimer, the term of this patent is extended or adjusted under 35 U.S.C. 154(b) by 987 days.

(21) Appl. No.: 15/994,592

(22) Filed: May 31, 2018

(65) Prior Publication Data

US 2019/0108310 A1 Apr. 11, 2019

(30) Foreign Application Priority Data

Oct. 6, 2017 (EP) ..................................... 17195217

(51) Int. Cl.
*G16B 30/00* (2019.01)
*G06F 17/16* (2006.01)
*G16B 30/10* (2019.01)

(52) U.S. Cl.
CPC ............. *G16B 30/00* (2019.02); *G06F 17/16* (2013.01); *G16B 30/10* (2019.02)

(58) Field of Classification Search
None
See application file for complete search history.

(56) References Cited

U.S. PATENT DOCUMENTS

| | | | | |
|---|---|---|---|---|
| 5,701,256 A | * | 12/1997 | Marr | G16B 30/00 702/20 |
| 2002/0049545 A1 | * | 4/2002 | Nishikawa | G16B 30/00 702/19 |
| 2003/0169926 A1 | * | 9/2003 | Sonmez | G16B 30/00 382/219 |
| 2005/0065969 A1 | * | 3/2005 | Thomas | G16B 50/00 |
| 2005/0196807 A1 | * | 9/2005 | Bulla, Jr. | G16B 30/10 435/6.13 |
| 2009/0119313 A1 | * | 5/2009 | Pearce | G06F 16/90344 |
| 2010/0299127 A1 | * | 11/2010 | Trabanino | G16B 15/00 703/11 |

(Continued)

FOREIGN PATENT DOCUMENTS

| | | | | |
|---|---|---|---|---|
| JP | 3395633 B2 | * | 4/2003 | ............ G06F 17/30 |
| WO | WO2021158989 | * | 2/2021 | ............ C12N 15/11 |

OTHER PUBLICATIONS

MACSE: Multiple Alignment of Coding SEquences Accounting for Frameshifts and Stop Codons, Ranwez et al., PLoS ONE | www.plosone.org Sep. 1, 2011 | vol. 6 | Issue 9 | e22594.*

Alignment of protein-coding sequences with frameshift extension penalties, Belanger et al., arXiv:1508.04783v1 [cs.DS] Aug. 19, 2015.*

(Continued)

*Primary Examiner* — David J Stoltenberg
(74) *Attorney, Agent, or Firm* — James Creighton Wray (57) ABSTRACT

The current invention concerns a computer-implemented method, a computer system and a tangible non-transitory computer-readable data carrier comprising a computer program product for aligning a query nucleic acid sequence against a reference nucleic acid sequence. An optimal alignment score of the query sequence against the reference sequence is determined by a dynamic programming algorithm. The algorithm is configured for locally optimizing a partial alignment score based on a nucleotide substitution cost, a gap insertion cost, an amino acid substitution cost, as well as a frameshift penalty.

15 Claims, 3 Drawing Sheets

(56) References Cited

U.S. PATENT DOCUMENTS

| | | | | |
|---|---|---|---|---|
| 2012/0215463 | A1* | 8/2012 | Brodzik | G16B 30/00 702/20 |
| 2012/0239706 | A1* | 9/2012 | Steinfadt | G16B 30/10 707/803 |
| 2012/0303472 | A1* | 11/2012 | Koehler | G06Q 30/0621 705/26.1 |
| 2013/0138358 | A1* | 5/2013 | Tang | G16B 30/00 702/20 |
| 2013/0184161 | A1* | 7/2013 | Kingsmore | C12Q 1/6869 506/2 |
| 2013/0324417 | A1* | 12/2013 | Kennedy | G16B 30/00 506/2 |
| 2013/0338934 | A1* | 12/2013 | Asadi | G16B 30/00 702/20 |
| 2015/0057946 | A1* | 2/2015 | Kural | G16B 30/00 702/20 |
| 2015/0197815 | A1* | 7/2015 | Kural | G16B 20/20 506/2 |
| 2015/0199472 | A1* | 7/2015 | Kural | C12Q 1/6869 506/2 |
| 2015/0315657 | A1* | 11/2015 | Rhodes | C12Q 1/6886 424/133.1 |
| 2016/0275240 | A1* | 9/2016 | Huelga | C12Q 1/6869 |
| 2016/0364523 | A1* | 12/2016 | Locke | G16B 30/00 |
| 2017/0154154 | A1* | 6/2017 | Daly | G16B 30/10 |
| 2018/0247016 | A1* | 8/2018 | Semenyuk | G16B 30/10 |
| 2019/0108310 | A1* | 4/2019 | Deforche | G16B 30/10 |

OTHER PUBLICATIONS

Aligning coding sequences with frameshift extension penalties, Jammali et al., Algorithms Mol Biol (2017) 12:10 DOI . 1186/s13015-017-0101-4.*

HMM-FRAME: accurate protein domain classification for metagenomic sequences containing frameshift errors, Zhang et al., BMC Bioinformatics 2011, 12:198 http://www.biomedcentral.com/1471-2105/12/198.*

Back-translation for discovering distant protein homologies in the presence of frameshift mutations, Gîrdea et al., Algorithms for Molecular Biology 2010, 5:6 http://www.almob.org/content/5/1/6.*

O. Gotoh, Journal of Molecular Biology 162, 705-708 (1982).

S.B. Needleman and C.D. Wunsch, Journal of Molecular Biology 48(3), 443-453 (1970).

T.F. Smith and M.S. Waterman, Journal of Molecular Biology 147, 195-197 (1981).

R.R. Stocsits, I.L. Hofacker, C. Fried and P.F. Stadler, BMC Bioinformatics 6, 160 (2005).

Hein, Jotun, An Alogorithm Combining DNA and Protein Alignment, Journal of Theoretical Biology. 1994 vol. 167, pp. 169-174.

Ranwez, Vincent, et. al. MACSE: Multiple Alignment of Coding Sequences Accounting for Frameshifts and Stop Codons, PLoS ONE 6(9):e22594. doi:10.1371/journal.pone.0022594.

Deforche, Koen, An Alignment Method for Nucleic Acid Sequences Against Annotated Genomes, bioRxiv preprint posted online Oct. 11, 2017;doi: http://dx.doi.org/10.1101.200394.

Jammali, Safa, et al. Aligning Coding Sequences With Frameshift Extension Penalties, Algorithms Molecular Biology. 2017. 12:10.

* cited by examiner

ALIGNMENT METHOD FOR NUCLEIC ACID SEQUENCES

The project leading to this application has received funding from the European Union's Horizon 2020 research and innovation program under grant agreement No. 634650.

TECHNICAL FIELD

The invention pertains to the technical field of bioinformatics, i.e. methods or systems for genetic or protein-related data processing in computational molecular biology. The invention pertains in particular to sequence comparisons involving nucleotides and/or amino acids (IPC G06F19/22).

BACKGROUND

"A general method applicable to the search for similarities in the amino acid sequence of two proteins", written by S. B. Needleman and C. D. Wunsch, published in the *Journal of Molecular Biology* 48(3), 443-453 (1970), doi:10.1016/0022-2836(70)90057-4 describes a dynamic programming algorithm to compare biological sequences based on a substitution cost and discusses further use of a gap penalization.

"Identification of Common Molecular Subsequences", written by T. F. Smith and M. S. Waterman, published in the *Journal of Molecular Biology* 147, 195-197 (1981), doi:10.1016/0022-2836(81)90087-5 describes a dynamic programming algorithm for determining similar regions between two strings of nucleic acid or amino acid sequences. Let $A=a_1a_2 \ldots a_n$ and $B=b_1b_2 \ldots b_m$ be the sequences to be aligned, with n and m the lengths of A and B, respectively. Let $S(a,b)$ be a pairwise substitution cost for elements a and b of sequences A and B, respectively. Let $W_k$ be the gap penalty for a gap of length k. In the Smith-Waterman algorithm, a scoring matrix H of size $(n+1) \times (m+1)$ is built. The first row and the first column are initialized to zero: $H_{k0}=0$ for $0 \leq k \leq n$ and $H_{0l}=0$ for $0 \leq l \leq m$. The scoring matrix is filled using the recursive equation $H_{ij}=\max(H_{i-1,j-1}+S(a_i, b_j); \max_{k \geq 1}\{H_{i-k,j}-W_k\}; \max_{l \geq 1}\{H_{i,j-l}-W_l\}; 0)$. Once the scoring matrix is filled, the best local alignment is generated by starting at the highest score in the scoring matrix H and tracing back the source of each recursively determined score, until a matrix cell with score 0 is reached. For an affine gap cost $W_k=u(k-1)+v$ (with $u>0$ and $v>0$), the computational cost of the Smith-Waterman algorithm is $O(m^2n)$.

"An improved algorithm for matching biological sequences", written by O. Gotoh, published in the *Journal of Molecular Biology* 162, 705-708 (1982), 10.1016/0022-2836(82)90398-9 describes an improvement on the Smith-Waterman algorithm in which an affine gap cost can be incorporated in the dynamic programming algorithm in O(mn) computational complexity.

U.S. Pat. No. 5,701,256 and US 2009/0 119 313 describe computer-implemented methods for the alignment of a sequence to a reference sequence.

"An algorithm combining DNA and protein alignment", written by J. Hein, published in the *Journal of Theoretical Biology* 167(2), 169-174 (1994), doi:10.1006/jtbi.1994.1062 discloses a dynamic programming algorithm considering nucleotide substitutions, amino acid substitutions, and insertions and deletions which are restricted to multiples of three. The document furthermore discloses the formulated programs in the document cannot handle overlapping reading frames, which is a serious shortcoming, as large scale DNA may contain a mix of coding, non-coding and possibly overlapping reading frames.

"Multiple sequence alignments of partially coding nucleic acid sequences", written by R. R. Stocsits, I. L. Hofacker, C. Fried and P. F. Stadler, published in *BMC Bioinformatics* 6, 160 (2005), doi:10.1186/1471-2105-6-160 describes codaln, a computer program product for the alignment of sequences.

"MACSE: Multiple Alignment of Coding Sequences Accounting for Frameshifts and Stop Codons", written by V. Ranwez, S. Harispe, F. Delsuc and E. J. P. Douzery, published in *PLoS ONE* 6(9), e22594 (2011), doi:10.1371/journal.pone.0022594 describes MACSE, a computer program product for the alignment of sequences.

"Aligning coding sequences with frameshift extension penalties", written by S. Jammali, E. Kuitche, A. Rachati, F. Bélanger, M. Scott and A. Ouangraoua, published in *Algorithms for Molecular Biology* 12:10 (2017), doi:10.1186/s13015-017-0101-4 ("Jammali et al.") discloses pairwise coding DNA sequence (CDS) alignment via a dynamic programming algorithm accounting for frameshift translation initiation and length, and considering nucleotide and amino acid sequences. The algorithm uses two dynamic programming tables, whereby an entry (i, j) depends on non-nearest-neighbor entries, i.e. on a subtable extending from (i−3, j−3) to (i, j). The algorithm is furthermore not adapted for sequences with a mix of coding, non-coding and possibly overlapping reading frames.

In a viable coding sequence, frameshifts are unexpected, but may occasionally occur as a consequence of sequencing errors. The computer-implemented methods disclosed in some of the above-cited documents result in an unrealistically large number of artificial frameshifts when used to align sequences with one or multiple open reading frames. The corresponding amino acid sequences thereby largely lose their biological meaning.

The present invention aims to resolve at least some of the problems mentioned above.

SUMMARY OF THE INVENTION

In a first aspect, the present invention provides a computer-implemented method for aligning a query nucleic acid sequence against a reference nucleic acid sequence, according to claim 1.

In a second aspect, the present invention provides a computer system for aligning a query nucleic acid sequence against a reference nucleic acid sequence, according to claim 10.

In a third aspect, the present invention provides a tangible non-transitory computer-readable data carrier comprising a computer program product for aligning a query nucleic acid sequence against a reference nucleic acid sequence, according to claim 11.

In a fourth aspect, the present invention provides a use of the computer-implemented method according to the first aspect for identification of an organism, preferably a pathogen, more preferably a RNA or DNA virus.

In a fifth aspect, the present invention provides a use of the computer-implemented method according to the first aspect for reconstructing a phylogenetic tree of a multitude of organisms from a plurality of nucleic acid sequences obtained from said multitude of organisms.

In a sixth aspect, the present invention provides a use of the computer-implemented method according to the first aspect for obtaining a contiguous sequence from a plurality of sequence fragments.

In a seventh aspect, the present invention provides a use of the computer-implemented method according to the first aspect for determining nucleic acid and/or amino acid substitutions for genotype-phenotype associations.

The present invention is advantageous because a dynamic programming algorithm which locally optimizes a partial alignment score based on a nucleotide substitution cost, an amino acid substitution cost, a gap insertion cost and a frameshift penalty not only mitigates the problem of an unrealistically large number of artificial frameshifts, but also yields the surprising result that sequence alignments of similar or better accuracy are obtained, in contrast to the expectation that higher constraints regarding frameshifts would worsen alignment.

The present invention is further advantageous as it allows to simultaneously match multiple, possibly partially overlapping and possibly oppositely oriented, coding sequences (reading frames) between a query and a reference nucleic acid sequence with a single recursive build-up of a two-dimensional array in a bottom-up approach in O(mn) computational complexity. The present invention thus allows for efficiently handling overlapping reading frames, and account for occasional frameshifts, and thereby provides a solution for the long-felt need stated by J. Hein (1994).

Furthermore, in the case of multiple coding sequence annotations, prior art methods could be executed for each coding sequence separately, leading to multiple alignments which may be treated further individually or somehow combined (e.g. concatenated). However, such an approach presents certain disadvantages:
- alignment becomes more accurate if the portions which are being aligned, are longer. This effect becomes more important if sequences have diverged further;
- phylogenetic methods work only on the basis of a single alignment. They also work better if there is a bigger phylogenetic signal, which depends linearly on the length of the alignment;
- methods as in Jammali et al. are incapable to align non-coding portions, which typically occur between different annotations. In general, a genomic construct is a combination of CDS and non-coding sequences. Hence, prior art methods clearly fall short.

The present invention concerns an alignment method wherein a reference sequence with
- multiple, i.e. two or more, coding sequence annotations and zero, one or more non-coding regions, and/or
- one or more coding sequence annotations and one or more non-coding regions can be compared to in a single alignment run as a whole, and thus allows to use all available information of the reference sequence to be used in an integrated approach, thereby overcoming the above shortcomings. For instance, the reference sequence may comprise:
- 2, 3, 4, 5 or more coding sequence annotations and zero non-coding regions;
- 1, 2, 3, 4, 5 or more coding sequence annotations and 1 non-coding region;
- 1, 2, 3, 4, 5 or more coding sequence annotations and 2 non-coding regions, or
- 3, 4, 5 or more non-coding regions and at least 2 coding sequence annotations.

Hence, in a preferred embodiment of the invention, the reference sequence comprises multiple coding sequence annotations and one or more non-coding regions, e.g.
- 2, 3, 4, 5 or more coding sequence annotations and 1 non-coding region;
- 2, 3, 4, 5 or more coding sequence annotations and 2 non-coding regions;
- 3, 4, 5 or more non-coding regions and at least 2 coding sequence annotations.

DETAILED DESCRIPTION OF THE INVENTION

The present invention concerns a computer-implemented method, a computer system, and a tangible non-transitory computer-readable data carrier comprising a computer program product for aligning a query nucleic acid sequence against a reference nucleic acid sequence. The present invention furthermore concerns several uses of the computer-implemented method. The present invention has been summarized in the corresponding section above. In what follows, the invention is described in detail, preferred embodiments are discussed, and the invention is illustrated by means of examples.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, elements, members, steps, known in the art or disclosed therein.

"Dynamic programming" is a method for solving a complex problem by breaking it down into a collection of simpler subproblems, solving each of those subproblems just once, and storing their solutions. The next time the same subproblem occurs, instead of recomputing its solution, one simply looks up the previously computed solution. Said storing can occur in a tangible transitory computer-readable storage medium and/or a tangible non-transitory computer-readable storage medium. A dynamic programming method is based on the principle of mathematical induction, and is a bottom-up approach which starts from the simplest sub-problems up towards the given problem. In this approach, it is guaranteed that the subproblems are solved before solving the given problem. An alternative method based on the principle of mathematical induction is a "memoization"

method, which is a top-down approach which starts from the given problem, and whereby subproblems are solved as they are encountered.

The recitation of numerical ranges by endpoints includes all numbers and fractions subsumed within that range, as well as the recited endpoints.

In a first aspect, the present invention provides a computer-implemented method for aligning a query nucleic acid sequence against a reference nucleic acid sequence. In a second aspect, the present invention provides a computer system for aligning a query nucleic acid sequence against a reference nucleic acid sequence. In a third aspect, the present invention provides a tangible non-transitory computer-readable data carrier comprising a computer program product for aligning a query nucleic acid sequence against a reference nucleic acid sequence. One of ordinary skill in the art will appreciate that the first, second and third aspects of the invention are interrelated. The computer system is configured for performing steps of the computer-implemented method, and the computer program product comprises instructions for performing steps of the computer-implemented method, for example by execution of the instructions on a computer system according to the second aspect. Therefore, in what follows no distinction will be made between the first, second and third aspects of the present invention.

An optimal alignment score of the query sequence against the reference sequence is determined by an algorithm. The algorithm is configured for locally optimizing a partial alignment score based on a nucleotide substitution cost, a gap insertion cost, an amino acid substitution cost, and a frameshift penalty in the query and reference sequences. The frameshift penalty is introduced for a number of consecutive gap insertions not divisible by three. The amino acid substitution cost is based on three consecutive nucleotides in the query sequence and three consecutive nucleotides in the reference sequence. Preferably, the nucleotide substitution cost is a pairwise nucleotide substitution cost. Preferably, the amino acid substitution cost is a pairwise amino acid substitution cost.

A non-limitative list of examples of algorithms comprises a dynamic programming algorithm, a memoization algorithm, a heuristic search with local extension, and a k-mer matching algorithm. Preferably said algorithm is a dynamic programming algorithm, which may allow retrieval of an optimal solution.

A nucleic acid sequence is a succession of symbols which indicate the order of nucleotides within at least a portion of a deoxyribonucleic acid (DNA) or ribonucleic acid (RNA) molecule. Preferably, the symbols comprise letters such as G, A, C and T for DNA molecules and G, A, C and U for RNA molecules. These letters denote the nucleotides guanine (G), adenine (A), cytosine (C), thymine (T) and uracil (U).

The sequence of nucleotides on a nucleic acid strand is translated by cell machinery into a sequence of amino acids making up a protein strand. A group of three nucleotides, called a codon, corresponds to either one amino acid or a stop codon. A nucleic acid sequence may hence comprise a codon sequence encoding an amino acid sequence corresponding to a protein.

Nucleic acid sequences may be obtained from biological material by any known extraction method and sequencing method. A non-limiting set of extraction and sequencing methods are discussed in, for example, U.S. Pat. No. 8,209,130. Nucleic acid sequences may also be obtained by artificial gene synthesis.

A nucleic acid sequence may be stored on a tangible non-transitory computer-readable storage medium in a computer-readable format, preferably in digital format. An often-used format for storing nucleic acid sequences is the FASTA format, a text-based format in which nucleotides are represented using single-letter codes. The format also allows for sequence names and comments. A non-limiting list of examples of sequence formats comprises the FASTA, FASTQ, NEXUS, Short Reach Archive (SRA) and Stockholm formats, the format disclosed in, for example, U.S. Pat. No. 5,856,928, and the like.

Sequence databases may store large quantities of such computer-readable nucleic acid sequences. A non-limiting list of examples of sequence databases comprises FlyBase, GenBank, the DNA DataBank of Japan, the Eukaryotic Pathogen Database (EuPathDB), the European Nucleotide Archive, the Influenza Research Database (IRD), the Pathogen-Host Interaction Database (PHI-base), the *Saccharomyces* Genome Database, the Virus Pathogen Database and Analysis Resource (ViPR), VectorBase, WormBase, and the like.

As the invention relates to a computer-implemented invention, "nucleic acid sequence" should be interpreted as "computer-readable nucleic acid sequence" or "nucleic acid sequence in computer-readable format", where appropriate. A computer-readable nucleic acid sequence is preferably provided in digital format on a tangible non-transitory computer-readable storage medium such as, for example, a hard disk drive, a solid state drive, a storage server, a storage cloud, and the like. At least a portion of the nucleic acid sequence may be read in from the tangible non-transitory computer-readable storage medium and placed in a tangible transitory computer-readable storage medium for processing according to the present invention, preferably via execution of computer-readable instructions via at least one central processing unit and thereby at least partially utilizing the nucleic acid sequence data placed in the tangible transitory computer-readable storage medium.

The optimal alignment score may be determined for an optimal local or global alignment. The present invention is advantageous because an algorithm which locally optimizes a partial alignment score based on a nucleotide substitution cost, an amino acid substitution cost, a gap insertion cost, and a frameshift penalty not only mitigates the problem of an unrealistically large number of artificial frameshifts, but also yields the surprising result that sequence alignments of similar or better accuracy are obtained, in contrast to the expectation that higher constraints regarding frameshifts would worsen alignment. Using a nucleotide substitution cost in conjunction with an amino acid substitution cost allows to align divergent coding nucleic acid sequences in addition to similar coding nucleic acid sequences. This requires the detection of correct open reading frames and is prone to eventual frameshift errors. When only amino acid substitutions are considered, the more sensitive evolutionary information within synonymous substitutions is however lost. By considering the possibility of (likely erroneous) insertions or deletions that cause frameshifts, the alignment score is suitable to align sequences obtained from sequencing techniques that are prone to such sequencing errors, without misusing frameshifts artificially as a means to optimize amino acid sequence similarity. In a preferred embodiment, the algorithm is a dynamic programming algorithm. The present invention thereby improves on the Needleman-Wunsch, Smith-Waterman, and Gotoh algorithms by expanding these dynamic programming algorithms with additional induction state parameters.

Figure 1:
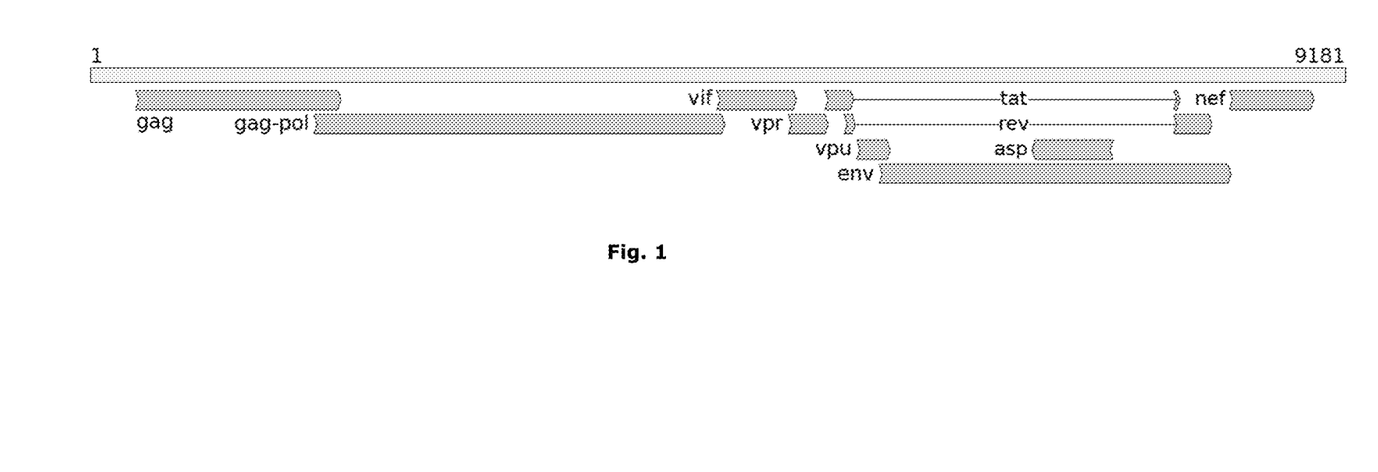
FIG. 1 shows a schematic overview of coding DNA sequence (CDS) annotations of HIV-1, as derived from the GenBank record NC_001802.

The reference (nucleic acid) sequence may comprise at least one coding sequence annotation. The coding sequence annotation represents a codon sequence encoding an amino acid sequence. Each coding sequence indicates the location of one or more regions in the reference sequence that jointly translate to a protein or polyprotein. Multiple codon sequences may hereby partially overlap, which is not unusual for compact viral genomes. A codon sequence may be part of the forward strand or the reverse complementary strand. The at least one coding sequence annotation may hence comprise an annotation for a forward coding sequence and an annotation for a reverse (complementary) coding sequence. An example of a coding sequence annotation is a coding DNA sequence (CDS) annotation from the GenBank sequence database. Several CDS annotations for HIV-1, as derived from the GenBank record NC_001802, are schematically depicted in FIG. 1.

In a preferred embodiment, the reference sequence comprises at least one coding sequence annotation. Preferably, said at least one coding sequence annotation comprises multiple coding sequence annotations. In this case, the reference sequence comprises multiple coding sequence annotations. Said multiple coding sequence annotations comprise at least two coding sequence annotations, such as two, three, four, five, six, seven, eight, nine, ten, eleven, twelve, thirteen, fourteen, fifteen, sixteen, seventeen, eighteen, nineteen, twenty, or more coding sequence annotations. The reference sequence may thereby comprise non-coding regions as well as coding regions. A coding region may comprise multiple at least partially overlapping coding sequence annotations. A coding region may comprise overlapping annotations for a forward and a reverse coding sequence. A coding sequence annotation is configured for deriving for a nucleotide if the nucleotide corresponds to the coding sequence. A nucleotide may thereby correspond to zero (non-coding region), one, two, three, four, five, or six coding sequences, and possibly even more than six coding sequences. Preferably, the reference sequence comprises at least one nucleotide, and preferably multiple nucleotides, each corresponding to two, three, four, five, six or more coding sequences. Hereby, note that more than six coding sequences are in principle possible, albeit very uncommon, in the case the resulting protein or polyprotein is the consequence of a different splice variant or slippage of polymerase during transcription. E.g. for HIV this is the case with 'gag' and 'gag-pol': in 'gag-pol' one can find the first part of 'gag' (which usually is not drawn as such, but is annotated as such). Hence, a specific nucleotide may belong up to maximally six different open reading frames, but is allowed to belong to more than six coding sequences. We further note that such a situation would be highly uncommon in practice.

This is advantageous as it allows to simultaneously match multiple, possibly partially overlapping and possibly oppositely oriented, coding sequences (reading frames) between a query and a reference nucleic acid sequence with a single recursive build-up of a two-dimensional array in a bottom-up approach. Note that with a pairwise alignment method of separate coding sequences (reading frames) no optimal global alignment for the complete query sequence against the complete reference sequence comprising multiple coding sequences can be obtained.

In addition to the above, the reference sequence may comprise multiple coding sequence annotations and one or more non-coding regions. The present invention presents the unique advantage over prior art methods to allow alignment against reference sequences comprising both coding sequences and non-coding regions.

The amino acid substitution cost may be taken into account when an amino acid (three consecutive nucleotides; codon) substitution is considered in between the query and reference nucleic acid sequences. In a preferred embodiment, said amino acid substitution cost is taken into account for each amino acid substitution in between the reference and query sequences for which the corresponding amino acid in the reference sequence is represented by a coding sequence annotation. Preferably, an amino acid substitution cost is taken into account for each corresponding amino acid in the reference sequence which is represented by a coding sequence annotation and for which a substitution in between the reference and query sequences is considered. Preferably, said amino acid substitution cost is taken into account only when the corresponding amino acid in the reference sequence is represented by a coding sequence annotation.

In a preferred embodiment, said frameshift penalty is taken into account within each sequence portion corresponding to a coding sequence annotation. Preferably, said frameshift penalty for a number of consecutive gap insertions not divisible by three in a sequence portion is accounted for each coding sequence annotation to which the sequence portion corresponds. For overlapping reading frames according to the at least one coding sequence annotation, it might hence occur that a gap results in multiple frameshift penalties.

In a preferred embodiment, the partial alignment score is further based on a misalignment penalty for each gap opening, i.e. a gap insertion in either of the query or the reference sequence which is adjacent to a nucleotide, which corresponds to a break-up of a codon represented by a coding sequence annotation. Preferably, said misalignment penalty is accounted for each broken-up codon represented by a coding sequence annotation. For overlapping reading frames, it might hence occur that a single gap insertion results in multiple misalignment penalties.

This is advantageous as the partial alignment score then reflects the functional alignment, i.e. the alignment due to identified and annotated coding sequences, to a higher degree. During evolution, non-functional sequence portions may alter with less repercussions. This is not the case for functional sequence portions, i.e. the sequence portions comprising a codon sequence encoding a viable amino acid sequence corresponding to a working protein of importance to an organism.

In a preferred embodiment, the dynamic programming algorithm is configured for recursively determining a two-dimensional array of induction states (IS) in a bottom-up approach. Thereby, each induction state comprises a partial alignment score, and corresponds to a query sequence length n (query portion of length n) and a reference sequence length m (reference portion of length m) ($IS_{n,m}$). An induction state of the array ($IS_{n,m}$) corresponding to query sequence length n and reference sequence length m is determined based on the induction states corresponding to each of the query and reference sequence length combinations n−1 and m; n−1 and m−1; and n and m−1 with both query and reference sequence lengths nonnegative.

This is advantageous as it allows for a local optimization of the partial alignment score, as the partial alignment score of an induction state can be determined based on the neighboring induction states. More specifically, $IS_{n,m}=f(IS_{n-1,m}; IS_{n-1,m-1}; IS_{n,m-1})$.

In a preferred embodiment, an induction state comprises a substitution score, three reference insertion scores, three query insertion scores, and a partial alignment score.

Thereby, the substitution score takes into account nucleotide and amino acid substitution costs. The three reference insertion scores take into account gap insertions as well as frameshift penalties in the reference sequence. Thereby, the frameshift penalty for a number of consecutive gap insertions not divisible by three can be taken into account by cyclic mapping of the reference insertion scores during said recursive determination. The three query insertion scores take into account gap insertions as well as frameshift penalties in the query sequence. Thereby, the frameshift penalty for a number of consecutive gap insertions not divisible by three can be taken into account by cyclic mapping of the query insertion scores during said recursive determination. The partial alignment score is the optimum of the three reference insertion scores, the three query insertion scores, and the substitution score of the same induction state.

In a preferred embodiment, an induction state comprises a first, a second and a third insertion score for a sequence. The induction state may comprise such three insertion scores for the reference sequence. The induction state may comprise such three insertion scores for the query sequence. The induction state may comprise such three insertion scores for each of the query and reference sequences. The first insertion score accounts for said sequence ending in a gap with a length for which the length modulo three is equal to one. The second insertion score accounts for said sequence ending in a gap with a length for which the length modulo three is equal to two. The third insertion score accounts for said sequence ending in a gap with a length for which the length modulo three is equal to zero. For a gap extension in the sequence, the first insertion score is based on the third insertion score augmented with a frameshift penalty per corresponding coding sequence annotation, the second insertion score is based on the first insertion score, and the third insertion score is based on the second insertion score subtracted with said frameshift penalty per corresponding coding sequence annotation. The frameshift penalty for a number of consecutive gap insertions not divisible by three is hence taken into account by cyclic mapping of the insertion scores during said recursive determination of said two-dimensional array of induction states (IS) in a bottom-up approach. For said gap extension in said sequence, each of said first, second and third insertion scores may be further based on a gap extension cost according to an affine gap model.

Once the two-dimensional array has been recursively determined, determination of the alignment score for the query sequence against the reference sequence comprises the step of selecting the optimal partial alignment score from said two-dimensional array of induction states. The corresponding sequence alignment can be retrieved by backtracing the source of a partial alignment score, i.e. which of the neighboring cells has led to the optimum of the partial alignment score.

In a preferred embodiment, all partial alignment scores and substitution scores of the induction states in the first row and the first column are initialized to zero. Preferably, all reference insertion scores and query insertion scores of the induction states in the first row and the first column are initialized to a large negative number, in absolute value smaller than any of the absolute values of the algorithmic parameters, most preferably initialized to minus infinity.

In a preferred embodiment, the gap insertion cost is an affine gap insertion cost, whereby the gap insertion cost depends on whether the gap is inserted adjacent to a nucleotide or adjacent to a previously inserted gap. Preferably, in addition an incremental amino acid open gap cost is added when opening the gap, and an amino acid gap extension cost is added for every additional three nucleic acid gaps.

In a preferred embodiment, an induction state additionally comprises backtrace information. This is advantageous as it allows for a quick determination of the alignment and as it does not require to store the entire two-dimensional array on a tangible transitory or non-transitory computer-readable storage medium.

In a preferred embodiment, the memory usage is optimized holding in memory only at least 2 columns or at least 2 rows, together with the necessary trace-back storage for the preceding columns or rows. Hence, preferably the memory usage is being optimized by not holding at one time the whole induction state table in memory.

In a preferred embodiment, output is provided. The output hereby comprises alignment information for the nucleic acid sequence and for each of the coding sequences. The alignment information comprises at least one, and preferably all, of the following parameters: the optimal alignment score, the coverage length, the number of substitutions, the number of matches, the number of insertions, the number of deletions, the number of frameshifts and the number of codon misalignments.

The first, second and third aspects of the present invention may be used for various purposes, such as:
  the assessment of similarity of a query sequence and a reference sequence, whereby the alignment score forms a quantitative similarity assessment which may be utilized for defining a distance measure;
  the simultaneous alignment of multiple query sequences against a reference sequence, which may, for example, be used for improved speed by loading the reference sequence from a tangible non-transitory storage medium (disk) less or only once in a tangible transitory storage medium (memory);
  the alignment of multiple sequences by:
    pairwise aligning all pairs of said multiple sequences according to the above disclosed aspects of the present invention, thereby yielding a distance or similarity for each pair;
    building a score matrix of distance or similarity of the pairs, indicating the divergence/similarities of each pair;
    building a guiding tree from the score matrix with branch length proportional to the score of each pair, said guiding tree comprising tips and a root; and
    aligning said multiple sequences by starting with the closest related pairs near the tips, aligning them, and then including other more distant pairs or sequences progressively towards the root of the guiding tree according to the branching order in the guide tree,
  the alignment of multiple sequences by:
    providing a reference sequence;
    aligning each of the multiple sequences pairwise against the reference sequence according to the above disclosed aspects of the present invention;
    merging the aligned multiple sequences in a multiple alignment; and
    optimizing the multiple alignment further where one or more of the multiple sequences comprise an insertion with respect to the reference sequence,
  identification of an organism, preferably a pathogen, more preferably a RNA or DNA virus, such as, for example, Adenovirus, alphavirus, aphthovirus, Arterivirus, Astrovirus, Borna disease virus, California encephalitis virus, canine distemper virus, canine parvovirus, cardiovirus, Corona virus, cow pox virus, coxsackievirus, cytomegalovirus, Dengue virus, Ebola virus, Enterovirus, Epstein-Barr virus, equine arteritis virus, erbovirus, hantavirus, Hepatitis B virus, hepatitis C virus, Hepatitis E virus, hepatovirus, Herpes simplex virus, HIV, infectious canine hepatitis virus, Influenzavirus A, influenzavirus B, influenzavirus C, isavirus, kobuvirus, Lymphocytic choriomeningitis virus, Marburg virus, Measles virus, monkey pox virus, mumps virus, Norwalk virus, orf virus, Papillomavirus, parechovirus, Parvovirus B19, poliovirus, polyomaviridae, Rabies virus, Reovirus, respiratory syncytial virus, rhinovirus, Rinderpest virus, rotavirus, Rubella virus, sheep pox virus, simian vacuolating virus, Smallpox virus, teschovirus, thogotovirus, Torque teno virus, vaccinia virus, varicella-zoster virus, and yellow fever virus;

medical diagnosis;

forensic biology;

reconstructing a phylogenetic tree of a multitude of organisms from a plurality of nucleic acid sequences obtained from said multitude of organisms;

obtaining a contiguous sequence from a plurality of sequence fragments;

determining nucleic acid and/or amino acid substitutions for genotype-phenotype associations, for e.g. interpretation of antibacterial or antiviral resistance;

microbiome analysis, for e.g. food chain monitoring and probiotics applications;

precision medicine;

vaccine design; and personalized vaccine design.

In another aspect of the present invention, the invention pertains to a sequencing system comprising:

a sequencing module for obtaining a query nucleic acid sequence from a biological sample;

a reference server comprising a database of reference nucleic acid sequences, the reference server configured for aligning a query nucleic acid sequence against a reference nucleic acid sequence by determining an optimal alignment score of the query sequence against the reference sequence by a dynamic programming algorithm configured for locally optimizing a partial alignment score based on a nucleotide substitution cost, a gap insertion cost and an amino acid substitution cost in the query and reference sequences, whereby the partial alignment score is further based on a frameshift penalty for a number of consecutive gap insertions not divisible by three, the reference server configured to thereby generate alignment data;

a processing module comprising a communication module for connecting the processing module to the reference server, the processing module configured for:

sending a query nucleic acid sequence obtained with the sequencing module to the reference server; and receiving alignment data from said reference server.

One of ordinary skill in the art will appreciate that all parts of the description, and all other aspects of the invention disclosed above also pertain to the sequencing system. The reference server may for example be a computer system according to the second aspect of the present invention, which further comprises a database of reference nucleic acid sequences against which a received query nucleic acid sequence can be aligned. Thereby the database may be local or remote. In a particularly preferred embodiment, the reference server is the computer system according to the second aspect of the present invention, which is in communication via the Internet with said database, which is preferably a public database (e.g. GenBank).

The invention is further described by the following non-limiting examples which further illustrate the invention, and are not intended to, nor should they be interpreted to, limit the scope of the invention.

EXAMPLES

Example 1: Dynamic Programming Algorithm

In this example, a preferred embodiment of a dynamic programming algorithm according to the present invention is disclosed in detail.

A reference nucleic acid sequence $G=g_1g_2 \ldots g_M$ and a query nucleic acid sequence $B=b_1b_2 \ldots b_N$ are provided in digital format.

The induction state $IS_{m,n}$ comprises eight scalars:

$$IS_{m,n}=[D_{m,n};M_{m,n};P^{(1)}_{m,n};P^{(2)}_{m,n};P^{(3)}_{m,n};Q^{(1)}_{m,n};Q^{(2)}_{m,n};Q^{(3)}_{m,n}].$$

For an alignment of $g_1g_2 \ldots g_m$ with $m \leq M$ and $b_1b_2 \ldots b_n$ with $n \leq N$:

$D_{m,n}$ is the best partial alignment score;

$M_{m,n}$ is the best score for an alignment ending with a substitution;

$P^{(g)}_{m,n}$ is the best score for an alignment ending with a gap of length $k=3i+g$ after $g_m$ in the reference sequence, with i a non-negative integer and g equal to 1, 2 or 3; and $Q^{(h)}_{m,n}$ is the best score for an alignment ending with a gap of length $k=3j+h$ after $b_n$ in the query sequence, with j a non-negative integer and h equal to 1, 2 or 3.

At each induction step m, n the induction state is updated using a computation of incremental scores:

$\Delta d_{m,n}$ is the incremental score for extending an alignment of $g_1g_2 \ldots g_{m-1}$ and $b_1b_2 \ldots b_{n-1}$ with a substitution;

$\Delta p_{m,n}(k)$ is the incremental score for extending an alignment of $g_1g_2 \ldots g_m$ and $b_1b_2 \ldots b_{n-1}$ by opening a gap (k=1) or extending a gap in the reference sequence to length k>1; and $\Delta q_{m,n}(k)$ is the incremental score for extending an alignment of $g_1g_2 \ldots g_{m-1}$ and $b_1b_2 \ldots b_n$ by opening a gap (k=1) or extending a gap in the query sequence to length k>1.

With these incremental scores, the induction state is then updated as follows:

$$M_{m,n}=D_{m-1,n-1}+\Delta d_{m,n};$$

$$P^{(1)}_{m,n}=\max[M_{m,n-1}+\Delta p_{m,n}(1);P^{(1)}_{m,n-1}+\Delta p_{m,n}(4)];$$

$$P^{(i)}_{m,n}=P^{(i-1)}_{m,n-1}+\Delta p_{m,n}(i) \text{ for } 2 \leq i \leq 3;$$

$$Q^{(1)}_{m,n}=\max[M_{m-1,n}+\Delta q_{m,n}(1);Q^{(1)}_{m-1,n}+\Delta q_{m,n}(4)];$$

$$Q^{(i)}_{m,n}=Q^{(i-1)}_{m-1,n}+\Delta q_{m,n}(i) \text{ for } 2 \leq i \leq 3; \text{ and}$$

$$D_{m,n}=\max[M_{m,n};P^{(1)}_{m,n};P^{(2)}_{m,n};P^{(3)}_{m,n};Q^{(1)}_{m,n};Q^{(2)}_{m,n};Q^{(3)}_{m,n}].$$

The M- and D-values of the induction states of the first row ($IS_{0,n}$; $0 \leq n \leq N$) and the first column ($IS_{m,0}$; $0 \leq m \leq M$) are initialized to zero. The P- and Q-values of the induction states of the first row ($IS_{0,n}$; $0 \leq n \leq N$) and the first column ($IS_{m,0}$; $0 \leq m \leq M$) are initialized to a large negative number, in absolute value much smaller than any of the (absolute values of the) algorithm parameters (see example 2), most preferably initialized to minus infinity. The scores of the other induction states are determined by means of the above outlined formulae.

For a local alignment, whenever a value $D_{m,n}$ is negative, the D- and M-values of $IS_{m,n}$ are set to zero and the P- and Q-values to said large negative number, said large negative number most preferably minus infinity. The optimum of the partial alignment scores within the two-dimensional array of induction states is determined: $D_{k,l}$. The corresponding optimal alignment is retrieved by tracking back the path through the induction state matrix from $IS_{k,l}$ until an induction state with partial alignment score equal to zero is reached.

The digital representation of the reference nucleic acid sequence also comprises at least one coding sequence annotation. The at least one coding sequence annotation may be represented as (or transformed to a representation comprising) a list of codons in which the nucleotide at position m participates: $C_m=\{[C_{m,1}, r_{m,1}],[c_{m,2}, r_{m,2}], \ldots, [c_{m,t}, r_{m,t}]\}$ where $1 \le c_{m,i} \le 3$, indicating the position of the nucleotide in a codon, and $r_{m,i}$ a Boolean indicating whether the codon is in the forward strand or in the reverse complementary strand. Thereby $t_m=|C_m|$ can be defined, the number of codons in which the nucleotide m takes part. A value of $t_m>1$ indicates that there are multiple overlapping coding sequences at the given nucleotide position m, possibly in different open reading frames.

The incremental score $\Delta d_{m,n}$ for extending an alignment of $g_1 g_2 \ldots g_{m-1}$ and $b_1 b_2 \ldots b_{n-1}$ with a substitution is calculated as:

$$\Delta d_{m,n} = W_{na}(g_m, b_n) + w_{aa} \sum_{1 \le i \le t_m} \chi_{m,n}(c_{m,i}, r_{m,i})$$

$W_{na}$ is the nucleic acid (na) substitution cost. $w_{aa}$ is a weight prefactor to scale the amino acid (aa) contribution relative to the nucleic acid (na) contribution. The sum component in the above equation adds the amino acid substitution score for each codon which starts at position m, and thus for which $c_{m,i}=1$:

$$\chi_{m,n}(c, r) = \begin{cases} W_{aa}(T_m(g, r), T_n(b, r)) & \text{if } c = 1 \\ 0 & \text{if } c \ne 1 \end{cases}$$

whereby $T_i(a,r)$ denotes the translation of the codon $a_i a_{i+1} a_{i+2}$ to an amino acid in the forward or the reverse complementary strand, depending on the value of r. In the above formula, $W_{aa}$ is the amino acid (aa) substitution cost.

The incremental score $\Delta p_{m,n}(k)$ for extending an alignment of $g_1 g_2 \ldots g_m$ and $b_1 b_2 \ldots b_{n-1}$ by opening a gap (k=1) or extending a gap in the reference sequence to length k>1 is calculated as:

$$\Delta p_{m,n}(k) = \Delta w_{na,k} + w_{aa} \sum_{1 \le i \le t_{m+1}} \eta_{m+1,n}(c_{m+1,i}, r_{m+1,i}, k)$$

whereby the nucleic acid gap increment $\Delta w_{na,k}=p_{u,na}$ for k>1 and $\Delta w_{na,k}=p_{v,na}$ for k=1, according to an affine gap model. The sum component in the above equation adds a score component $\eta$ for each annotated amino acid sequence which may be affected by the gap:

$$\eta_{m,n}(c,r,k) = v_{m,n}(c,r,k) + \omega(k) + \phi(k)$$

The codon breakage cost v undoes an amino acid substitution weight previously added at the beginning of the codon, plus adds a misalignment penalty $p_m$:

$$v_{m,n}(c, r, k) = \begin{cases} -W_{aa}(T_{m-c+1}(g, r), T_{n-c+1}(b, r)) + p_m & \text{if } c \ne 1 \text{ and } k = 1 \\ 0 & \text{if } c = 1 \text{ or } k \ne 1 \end{cases}$$

An incremental amino acid open gap cost is added when opening the gap, and an amino acid gap extension cost is added for every additional three nucleic acid gaps:

$$\omega(k) = \begin{cases} \Delta w_{aa,(k-1)/3+1} & \text{if } (k \bmod 3) = 1 \\ 0 & \text{if } (k \bmod 3) \ne 1 \end{cases}$$

whereby the amino acid gap increment $\Delta w_{aa,k}=p_{u,aa}$ for k>1 and $\Delta w_{aa,k}=p_{v,aa}$ for k=1, according to an affine gap model.

A frameshift penalty is incrementally updated based on the length of the gap k:

$$\phi(k) = \begin{cases} p_f & \text{if } (k \bmod 3) = 1 \\ 0 & \text{if } (k \bmod 3) = 2 \\ -p_f & \text{if } (k \bmod 3) = 0 \end{cases}$$

In an analogous fashion, the incremental score for opening or extending a gap in the query sequence can be defined:

$$\Delta q_{m,n}(k) = \Delta w_{na,k} + w_{aa} \sum_{1 \le i \le t_m} \eta_{m,n+1}(c_{m,i}, r_{m,i}, k)$$

Figure 2:
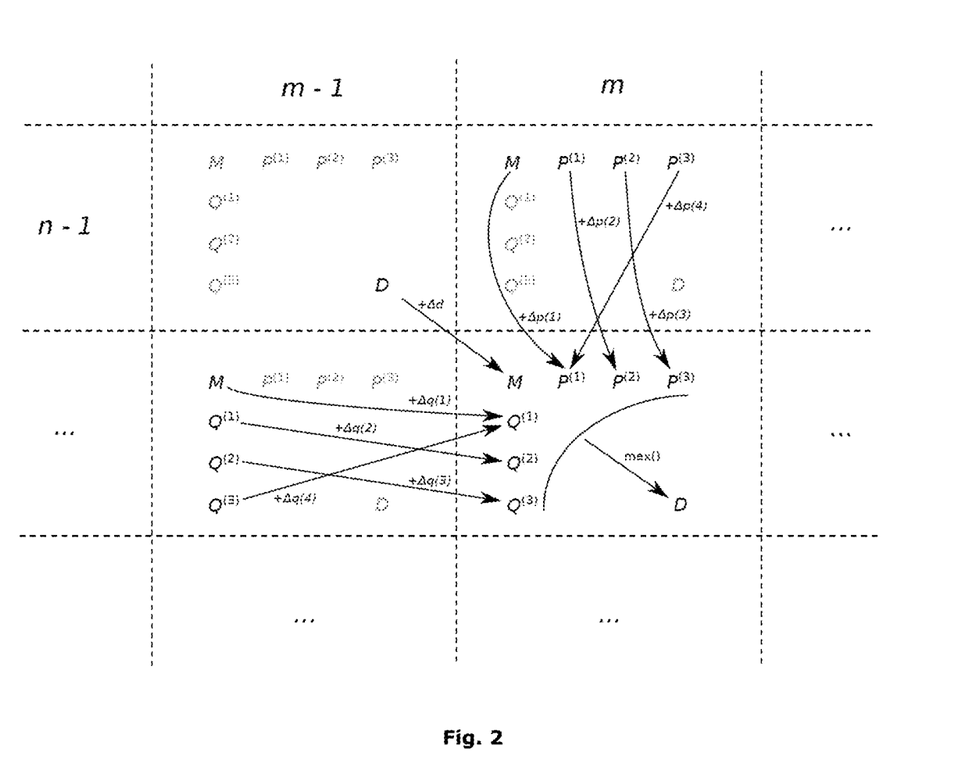
FIG. 2 shows a schematic overview of a recursive bottom-up determination of an induction state via a preferred embodiment of a dynamic programming algorithm according to the present invention.

The dynamic programming algorithm presented above is schematically depicted in FIG. 2.

The following features can be observed in the above dynamic programming algorithm:

For a nucleic acid sequence alignment $A_{na}(G,B)$, a genome alignment (ga) score $S_{ga}$ is defined based on a nucleic acid (na) alignment score $S_{na}$ and an amino acid (aa) alignment score $S_{aa}$, whereby the latter is weighted with the weight prefactor $w_{aa}$:

$$S_{ga}\{A_{na}(G,B)\} = S_{na}\{A_{na}(G,B)\} + w_{aa} S_{aa}\{A_{aa}(X,Y)\}$$

for each amino acid sequence alignment $A_{aa}(X,Y)$ that results from translation of the aligned sequences G and B according to the coding sequence annotations of G.

Each of the alignment scores $S_{na}$ and $S_{aa}$ comprises a component according to a substitution weight matrix W, and a gap component according to an affine gap model: $w_k = p_u(k-1) + p_v$ (with $p_v \le 0$ the penalty for opening a gap and $p_u \le 0$ the cost for extending a gap). Thereby, a gap of length k in the nucleic acid sequence with $3(n-1) < k \le 3n$ is considered a gap of length n in the amino acid sequence.

A misalignment penalty $p_m \le 0$ is added whenever a gap starts within a codon, disrupting proper translation of that codon. More formally, a misalignment penalty $p_m \le 0$ is added whenever a gap opens after position $g_m$, either in the query or reference sequence, when $C_m$ contains a codon position $c_{m,i} \ne 3$.

The amino acid sequence alignment score $S_{aa}$ by itself does not consider insertions and deletions in the underlying nucleic acid sequence that do not occur in a multiple of three. These however cause frameshifts which change the translation profoundly and thus have a large impact on the amino acid sequence alignment. Frameshifts are unexpected in a viable coding sequence, but they are not uncommon as a consequence of sequencing errors and thus their possibility (with low probability) needs to be considered to obtain a better alignment. The introduction of a frameshift needs thus to be weighted against the quality of the amino acid sequence alignment. In the genome alignment score, a frameshift penalty $p_f \leq 0$ is added for a gap of length k with (k mod 3)≠0.

Example 2: Implementation

Example 2 concerns the implementation and provision of a dynamic programming algorithm according to the present invention. Example 2 thereby preferably extends upon the dynamic programming algorithm outlined in example 1, but may also concern other implementations of dynamic programming algorithms according to the present invention.

The dynamic programming algorithm may be implemented as a standalone command-line tool in any known programming language. A non-limiting list of programming languages comprises C, C++, Java, Fortran, Pascal, and the like. Preferably, the standalone command-line tool is implemented in C++ 11.

The dynamic programming algorithm may additionally or alternatively be provided as a web application utilizable via a web interface which is accessible via a web browser and an Internet connection. The web interface may be implemented in html. The web interface may be configured to obtain input parameters, a query sequence, and a reference sequence from a user. The dynamic programming algorithm may be executed based on the obtained input parameters, the query sequence and the reference sequence on a server. Preferably, the server calls said standalone command-line tool.

Preferably, the reference genome should be provided in the form of a GenBank record, preferably comprising CDS annotations. Preferably, the query sequence should be provided in FASTA format.

The implementation encodes backtrace information within the induction state variables. This is advantageous as it does not require to keep the entire induction state matrix in memory. This renders the implementation suitable for sequence lengths up to $10^6$ nucleotides.

Example 3: Example Parameters

Example 3 concerns example parameters for the dynamic programming algorithm as outlined in example 1, and which may be implemented according to the provisions of example 2. They may be passed to the standalone command-line tool according to example 2 as command-line parameters.

An example set of parameters for the nucleic acid alignment score is:
$p_{v,na} = -10$
$p_{u,na} = -1$
$W_{na} = +2$ for a match of nucleic acids, and −2 for a mismatch of nucleic acids An example set of parameters for the amino acid alignment score is:
$w_{aa} = 1$
$p_{v,aa} = -6$
$p_{u,aa} = -2$
$W_{aa} = $ BLOSUM62
$p_f = -100$
$p_m = -20$ BLOSUM is an abbreviation for BLOcks Substitution Matrix for the sequence alignment of proteins via pairwise amino acid substitution. They were first described in "Amino Acid Substitution Matrices from Protein Blocks", written by S. Henikoff and J. G. Henikoff, published in PNAS 89(22), 10915-10919 (1992), doi: 10.1073/pnas.89.22.10915.

Figure 3:
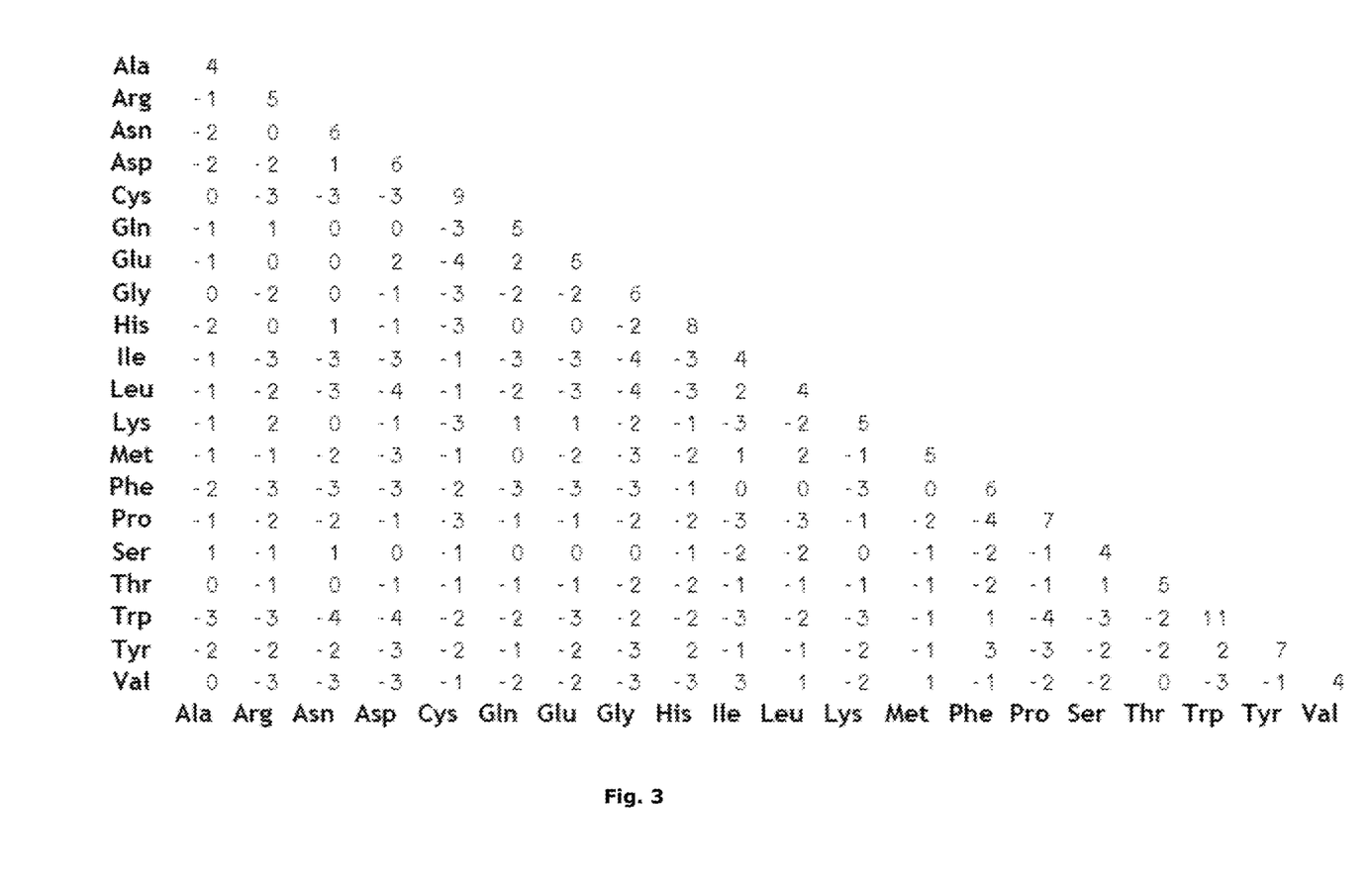
FIG. 3 shows the values of the BLOSUM62 matrix.

Examples of BLOSUM matrices are BLOSUM30, BLOSUM45, BLOSUM62 and BLOSUM80. Each value of the BLOSUM62 matrix, for example, is calculated by dividing the frequency of occurrence of the amino acid pair in the BLOCKS database, clustered at the 62% level, divided by the probability that the same two amino acids might align by chance. The ratio is then converted to a logarithm and expressed as a log odds score. BLOSUM matrices are usually scaled in half-bit units. A score of zero indicates that the frequency with which a given two amino acids were found aligned in the database was as expected by chance, while a positive score indicates that the alignment was found more often than by chance, and negative score indicates that the alignment was found less often than by chance. The BLOSUM62 matrix is shown in FIG. 3.

Example 4: Test Calculations

This example concerns test calculations with a dynamic programming algorithm as outlined in example 1 and as implemented as a standalone command-line program according to example 2. For some of the test calculations, the parameters according to example 3 are used. Where the parameters differ, it is explicitly noted below.

The test calculations are performed for each of the query sequences hiv1b, hiv1c, siv and hiv2 shown in Table 1 and the reference sequence HIV-1 (shown in Table 1 as well as FIG. 1). The reference sequence HIV-1 (Table 1; FIG. 1) comprises a multitude of coding sequences, some of which are in the reverse complementary strand, and some of which at least partially overlap.

TABLE 1

Sequences for the test calculations of Example 4.

| Name | Accession | Length | Description |
|------|-----------|--------|-------------|
| HXB2 | NC 001802 | 9181 | HIV-1 reference strain (Subtype B) |
| hiv1b | AY835761 | 9824 | HIV-1 Subtype B complete genome |
| hiv1c | U46016.1 | 9031 | HIV-1 Subtype C complete genome |
| Siv | KF304708.1 | 9449 | SIV complete genome |
| hiv2 | KP890355.1 | 9480 | HIV-2 complete genome |

Comparative calculations have been performed with the computer programs EMBOSS needle 6.6.0, MACSE 0.9b1 and codaln 1.0. The latter two have been described in the background section. Documentation on EMBOSS needle can be found in "EMBOSS: the European Molecular Biology Open Software Suite", written by P. Rice, I. Longden and A. Bleasby, published in Trends Genet. 16(6), 276-277 (2000). The configuration of these computer programs is shown in Table 2.

TABLE 2

Command-line arguments for the comparative calculations of Example 4.

| Name | Configuration |
|------|---------------|
| Needle | -gapopen 10 -gapextend 1 -datale EDNASIMPLE2 |
| MACSE | -g -10 -x -1 -f -100 -d 1 -s -10 |
| Codaln | -go 10 -gx 1 -m0 2 -m1 2 |

To evaluate the quality of each alignment, the number of frameshifts introduced within the coding sequences (#FS), the number of amino acids not aligned at a codon boundary (#MA), the affine gap model score for the nucleic acid sequences (NT score), and the sum of the affine gap model scores for all annotated amino acid sequences excluding frameshift and misalignment penalties (AA score) have been calculated. These are shown in Table 3. The present algorithm and implementation are denoted as "present", and where the parameters differ from Example 3, they are indicated in brackets. Runtimes are compared in Table 4.

TABLE 3

Results of the test calculations of Example 4.

| Sequence | Algorithm | # FS | # MA | NT score | AA score |
|---|---|---|---|---|---|
| hiv1b | present | 0 | 10 | 16182 | 18130 |
|  | present ($p_m = 0$) | 0 | 18 | 16190 | 18126 |
|  | present ($p_f = 0$) | 2 | 11 | 16193 | 18143 |
|  | needle | 3 | 20 | 16219 | 18054 |
|  | MACSE | 13 | 29 | 15521 | 18013 |
|  | codaln | 3 | 16 | 15615 | 18035 |
| hiv1c | present | 1 | 19 | 12478 | 16127 |
|  | present ($p_m = 0$) | 1 | 35 | 12501 | 16138 |
|  | present ($p_f = 0$) | 3 | 21 | 12477 | 16135 |
|  | needle | 22 | 54 | 12525 | 16097 |
|  | MACSE | 13 | 42 | 11772 | 15813 |
|  | codaln | 4 | 21 | 11930 | 15907 |
| siv | present | 2 | 23 | 1497 | 8536 |
|  | present ($p_m = 0$) | 2 | 124 | 1635 | 8705 |
|  | present ($p_f = 0$) | 64 | 75 | 1668 | 8699 |
|  | needle | 146 | 298 | 1980 | 8159 |
|  | MACSE | 13 | 66 | 62 | 8301 |
|  | codaln | 5 | 38 | 34 | 7552 |
| hiv2 | present | 1 | 30 | 1164 | 8080 |
|  | present ($p_m = 0$) | 2 | 134 | 1233 | 8269 |
|  | present ($p_f = 0$) | 56 | 69 | 1251 | 8242 |
|  | needle | 161 | 338 | 1650 | 7472 |
|  | MACSE | 18 | 78 | 213 | 7799 |
|  | codaln | 1 | 27 | −85 | 6983 |

TABLE 4

Runtime comparison for aligning hiv1b against HXB2 on a Dell XPS (Intel Core i7-7500U CPU at 2.70 GHz).

| Algorithm | Runtime (s) |
|---|---|
| present | 6.3 |
| needle | 4.5 |
| MACSE | 185.2 |
| codaln | 5.5 |

The computer programs which are compared in table 3 all use a dynamic programming induction matrix to compute an optimal alignment subject to a scoring function. Different results are caused by different assumptions embedded in their scoring functions. Of these computer programs, only the present invention and codaln take into account both nucleic acid substitution and amino acid substitution.

Codaln implements an algorithm which, like the embodiment disclosed in examples 1 and 2 according to the present invention, can read the annotations of coding sequences from a GenBank record. To align an unknown query sequence against an annotated genome, codaln will first search for open reading frames in the query sequence, which are used in a second step in the scoring function of a dynamic programming alignment algorithm. Codaln does not penalize frameshifts. Analysis of the results (table 3) showed that the lower alignment scores, and erroneous frameshifts, of codaln's alignments were caused by errors in these estimated open reading frames.

The present invention is advantageous because a dynamic programming algorithm which locally optimizes a partial alignment score based on a nucleotide substitution cost, an amino acid substitution cost, a gap insertion cost, and a frameshift penalty not only mitigates the problem of erroneous frameshifts, but also yields the surprising result that sequence alignments of similar or better accuracy are obtained, in contrast to the expectation that higher constraints regarding frameshifts would worsen alignment.

The invention claimed is:

1. Computer-implemented method for aligning a query nucleic acid sequence against a reference nucleic acid sequence, comprising the step of determining an optimal alignment score of the query sequence against the reference sequence by a dynamic programming algorithm, the algorithm configured for locally optimizing a partial alignment score based on a nucleotide substitution cost, a gap insertion cost, an amino acid substitution cost, and a frameshift penalty in the query and reference sequences, whereby the frameshift penalty is introduced for a number of consecutive gap insertions not divisible by three, wherein the reference sequence comprises:
   multiple coding sequence annotations, and/or
   one or more coding sequence annotations and one or more non-coding regions,
   wherein a coding sequence annotation representing represents a codon sequence encoding an amino acid sequence,
   wherein said amino acid substitution cost is taken into account for each amino acid substitution in between the reference and query sequences for which the corresponding amino acid in the reference sequence is represented by a coding sequence annotation,
   wherein said frameshift penalty is taken into account within each sequence portion corresponding to a coding sequence annotation,
   wherein the algorithm is configured for recursively determining a two-dimensional array of induction states corresponding to query and reference sequence lengths,
   wherein an induction state of the array corresponding to query sequence length n and reference sequence length m is determined based on the induction states corresponding to each of the query and reference sequence length combinations n−1 and m; n−1 and m−1; and n and m−1 with both query and reference sequence lengths nonnegative, wherein the induction state comprises a partial alignment score, wherein the induction state comprises a first, a second and a third insertion score for a sequence, for each of the query and reference sequences, accounting for said sequence ending in a gap with length modulo three equal to, respectively, one, two and zero,
   wherein for a gap extension in said sequence:
   the first insertion score is based on the third insertion score augmented with a frameshift penalty per corresponding coding sequence annotation,
   the second insertion score is based on the first insertion score; and
   the third insertion score is based on the second insertion score subtracted with said frameshift penalty per corresponding coding sequence annotation.

2. Computer-implemented method according to claim 1, wherein said reference sequence comprises at least partially overlapping coding sequence annotations.

3. Computer-implemented method according to claim 1 or 2, wherein said reference sequence comprises multiple coding sequence annotations and one or more non-coding regions.

4. Computer-implemented method according to claim 1 or 2, wherein the partial alignment score is further based on a misalignment penalty for each gap insertion in either of the query or the reference sequence which is adjacent to a nucleotide and corresponds to a break-up of a codon represented by a coding sequence annotation.

5. Computer-implemented method according to claim 1 or 2, wherein the multiple coding sequence annotations comprise an annotation for a forward coding sequence and an annotation for a reverse coding sequence.

6. Computer-implemented method according to claim 1, wherein an induction state comprises:
- a substitution score for taking into account nucleotide substitution costs and amino acid substitution costs;
- three reference insertion scores for taking into account frameshift penalties for gap insertions in the reference sequence by cyclic mapping of the reference insertion scores during said recursive determination;
- three query insertion scores for taking into account frameshift penalties for gap insertions in the query sequence by cyclic mapping of the query insertion scores during said recursive determination; and
- a partial alignment score, which corresponds to the optimum of the three reference insertion scores, the three query insertion scores and the substitution score of the induction state comprising said partial alignment score.

7. Computer-implemented method according to claim 1, wherein a determination of an alignment score for the query sequence against the reference sequence comprises a step of selecting optimal partial alignment score from a two-dimensional array of induction states.

8. Computer-implemented method according to claim 1, wherein a nucleotide substitution cost is a pairwise nucleotide substitution cost and wherein said amino acid substitution cost is a pairwise amino acid substitution cost.

9. Computer-implemented method according to claim 1, wherein a gap insertion cost depends on whether a gap is inserted adjacent to a nucleotide or adjacent to a previously inserted gap.

10. Computer system for aligning a query nucleic acid sequence against a reference nucleic acid sequence, wherein the computer system is configured for executing the method according to claim 1.

11. Tangible non-transitory computer-readable data carrier comprising a computer program product for aligning a query nucleic acid sequence against a reference nucleic acid sequence, the computer program product comprising instructions which, when the computer program product is executed by a computer, cause the computer to carry out the method according claim 1.

12. Use of the computer-implemented method according to claim 1 for identification of an organism, a pathogen, an RNA orDNA virus.

13. Use of the computer-implemented method according to claim 1 for reconstructing a phylogenetic tree of a multitude of organisms from a plurality of nucleic acid sequences obtained from said multitude of organisms.

14. Use of the computer-implemented method according to claim 1 for obtaining a contiguous sequence from a plurality of sequence fragments.

15. Use of the computer-implemented method according to claim 1 for determining nucleic acid and/or amino acid substitutions for genotype-phenotype associations.

\* \* \* \* \*